United States Patent [19]

Di Stazio et al.

[11] Patent Number: 4,619,916

[45] Date of Patent: Oct. 28, 1986

[54] TRIPEPTIDE COMPOUNDS CONTAINING PYROGLUTAMIC ACID AND TRYPTOPHAN, PROCESS FOR THEIR PRODUCTION AND THERAPEUTIC APPLICATIONS

[75] Inventors: Giovanni Di Stazio; Vincenzo Politi; Andrea Margonelli; Giovanna De Luca; Mario Materazzi, all of Rome, Italy

[73] Assignee: Polifarma S.p.A., Rome, Italy

[21] Appl. No.: 679,477

[22] Filed: Dec. 7, 1984

[51] Int. Cl.$^4$ .......................... A61K 37/02; C07K 5/08
[52] U.S. Cl. ........................................ 514/18; 530/331
[58] Field of Search ..................... 260/112.5 R; 514/18

[56] References Cited

PUBLICATIONS

Chem. Abstr., vol. 65, (1966) 2497.
Chem. Abstr., vol. 77, (1972) 135449p.
Chem. Abstr., vol. 82, (1975) 12523d.
Chem. Abstr., vol. 96 (1982) 200170z.
J. Med. Chem. (1972), vol. 15, 8–11, 222–226, 623–627.

Primary Examiner—Delbert R. Phillips
Attorney, Agent, or Firm—Cushman, Darby & Cushman

[57] ABSTRACT

Thirteen new tripeptides made from levorotatory amino acids are described, corresponding to the formula p—GLU—X—TRP X is a specific amino acid different from p-GLU and TRP, as well as a process for the preparation of these compounds, pharmaceutical formulations containing them and the use of these formulations as hypotensive and analgesic agents.

10 Claims, No Drawings

TRIPEPTIDE COMPOUNDS CONTAINING PYROGLUTAMIC ACID AND TRYPTOPHAN, PROCESS FOR THEIR PRODUCTION AND THERAPEUTIC APPLICATIONS

The present invention refers to new tripeptide compounds made from levorotatory amino acid, characterized by the presence of pyroglutamic acid as the NH$_2$-terminal acid, tryptophan as the COOH-terminal acid, and a third amino acid bonded to said terminal acids.

The present invention also refers to a process for the production of said compounds, pharmaceutical compositions containing them, and their use as hypotensive and analgesic agents.

BACKGROUND OF THE INVENTION

It is widely known in the literature that many peptides which act as neurotransmitters in the central nervous system or as releasing factors at the hypothalmic level are characterized by the presence of cyclized glutamic acid (p-GLU) as the NH$_2$-terminal amino acid.

For example, neurotensin, a 13 amino acid peptide present in all high order animals, has the initial sequence: p-GLU-LEU-TYR .... The releasing factor of the luteinizing hormone is a decapeptide characterized by the initial sequence p-GLU-HIS-TRP .... The releasing factor of thyrotropin is a tripeptide of structure p-GLU-HIS-PRO-NH$_2$. Human gastrin is a 17 amino acid peptide with initial sequence: p-GLU-GLY-PRO .... Research on pharmacologically active peptides extracted from amphibian skin or snake venom had led to the interesting discovery that most of these substances are characterized by the presence of p-GLU as NH$_2$-terminal amino acid. In effect, physalemin, heledoisin, cerulein, xenopsin, ranatensin, and bombesin are small peptides active at the vasal level with p-GLU as the NH$_2$-terminal acid. On the other hand, the work of Ondetti (Biochemistry 10, 4033 (1971)) and Kato (Biochemistry 10, 972 (1971)) identified 15 peptides from snake venom, all with p-GLU as the NH$_2$-terminal amino acid. Kato also described (Esperientia 22, 49 (1966)) the presence of tripeptides in some snake venoms: p-GLU-ASN-TRP and p-GLU-GLN-TRP, although no pharmacological activity was mentioned. Even though it is a characteristic common to many pharmacologically active peptides, the presence of p-GLU as NH$_2$ terminal amino acid has never been correlated with particular physiological effects.

SUMMARY OF THE INVENTION

It has now been discovered that some tripeptides with pyroglutamic acid as the NH$_2$-terminal acid and tryptophan as the COOH-terminal acid as well as their lower alkyl tryptophan esters can act as hypotensive and analgesic pharmaceutical agents.

The compounds according to the present invention are represented by the formula

p-GLU-X-TRP and X is selected from the class of radicals derived from: GLY, VAL, GLU, ASP, SER, ALA, ASN, GLN, ILE, LEU, PRO, LYS and ARG, in which:
GLU=glutamic acid
ASP=aspartic acid
GLN=glutamine
ASN=asparagine
p-GLU=pyroglutamic acid
LYS=lysine
arg=arginine
SER=serine
ILE=isoleucine
LEU=leucine
PRO=proline
GLY=glycine
ALA=alanine
TRP=tryptophan
VAL=valine Of these 15 peptides, those in which X=ASN and X=GLN are known in the literature, although their therapeutic activity is not. The other 13 peptides are new compounds.

According to the present invention the process for the production of compounds p-GLU-X-TRP comprises the operations of:

(a) reacting by liquid phase condensation, a leverotatory p-GLU acid, with a levorotatory amino acid X, where X is as described above, protected so as to obtain a dipeptide p-GLU-X, protected by the protecting groups for p-GLU-X and X;

(b) transforming the p-GLU-X, protecting group into an azide;

(c) reacting by liquid phase condensation the product of the preceeding operation (b) with TRP protected so as to give the tripeptide p-GLU-X-TRP in which the individual groups are bonded to one another by peptide bonds, and which has protecting groups; and (d) removing the protecting groups from p-GLU-X-TRP and recovering the tripeptide so produced.

The protecting groups are groups which are introduced to protect the selected function of the amino acid from undesired reactions. These groups must be easy to remove when the reaction is complete. Examples of protecting groups for the carboxyl function include methyl, ethyl, benzyl, p-nitrobenzyl. The process according to the present invention thus also gives the lower alkyl esters of tryptophan, in particular the methyl or ethyl tryptophan ester of said peptides. Examples of protecting groups for the amine function include benzyloxycarbonyl, tert-butoxycarbonyl and trifluoroacetyl. The techniques for introducing and removing these protecting groups are widely known by experts in the field.

The process according to the invention is carried out in the liquid phase; a particularly preferred solvent is N,N-dimethylformamide (DMF).

Object of the present invention are also pharmaceutical compositions containing compounds p-GLU-X-TRP, or the lower alkyl tryptophan esters thereof, and the use of these pharmaceutical compositions as hypotensive and analgesic agents.

DETAILED DESCRIPTION OF THE INVENTION

Examples of the process for producing the individual compounds are given below.

EXAMPLE 1

Synthesis of p-GLU-GLY-TRP 1 g of the o-pentachlorophenylester of pyroglutamic acid (n-GLU-O-PCP) dissolved in dimethylformamide (DMF) is additioned, under stirring, with 0.326 g of glycine methyl ester hydrochloride (GLY-OMe-HCl), dissolved in DMF and 0.5 ml of Et$_3$N.

The resulting mixture is stirred for 24 hours at room temperature. Purification on silica gel affords 0.339 g of dipeptide p-GLU-GLY-OMe. This is reacted with an excess hydrazine hydrate and, after crystallization, 0.258 g of hydrazine derivative p-GLU-GLY-NH-NH$_2$ are obtained. The corresponding azide p-GLU-GLYN$_3$ is prepared by reaction with isopentylnitrite for 30 minutes at 20° C. This is then reacted 'with situ' with 0.304 g of tryptophan methylester hydrochloride (TRP-OMe.HCl) in DMF and 0.15 ml of Et$_3$N, by stirring for 24 hours at room temperature. Purification on a silica gel column affords 0.361 g of protected tripeptide p-GLU-GLY-TRP-OMe. Mild hydrolysis in basic solution affords 0.283 g of p-GLU-GLY-TRP.

Composition: theoretical: C=58.27, H=5.41, N=15.03. Found: C=58.01, H=5.22, N=15.09.

Melting point: 262° C.

EXAMPLE 2

Synthesis of p-GLU-VAL-TRP 1 g of p-GLU-OPCP is additioned, under stirring, with 0.436 g of valine methylester hydrochloride (VAL-OMe.HCl) dissolved in DMF and 0.5 ml of Et$_3$N. Stirring is continued for 24 hours at room temperature. Purification on silica gel affords 0.392 g of dipeptide p-GLU-VAL-OMe. This is reacted with hydrazine hydrate, and after crystallization affords 0.303 g of the hydrazine derivative pGLU-VAL-NH-NH$_2$. The corresponding azide is prepared by reaction of this compound with isopentylnitrite for 30 minutes at 20° C. The resulting product is then additioned with 0.293 g of tryptophan methylester hydrochloride (TRP-OMe.HCl) in DMF and 0.15 ml of Et$_3$N, stirring the mixture for 24 hours at room temperature. Purification on silica gel affords 0.366 g of protected tripeptide pGLU-VAL-TRP-OMe. After mild hydrolysis under basic conditions, purification affords 0.293 g of the free tripeptide pGLU-VAL-TRP.

Composition: theoretical: C=60.86, H=6.32, N=13.51. Found: C=60.96, H=6.41, N=13.42.

Melting point: 265° C.

EXAMPLE 3

Synthesis of pGLU-GLU-TRP 1 g of tryptophan methyl ester hydrochloride (TRP-OMe-HCl) in DMF is additioned with 0.4 ml of Et$_3$N and stirred for 30 minutes. The solution is then cooled to −10° C. and treated, in succession, with 1.322 g of Z-GLU-(Bu$^t$)$_5$-OH (Z=carbobenzoxy, Bu$^t$=tertiary butyl) in DMF, 0.530 g of hydroxybenzotriazol (HOBT) and 1.238 g of dicyclohexylcarbodiimide (DCCI). This is kept at −10° C. for the first three hours, and then at room temperature for another 28 hours. Purification on silica gel affords 1.266 g of protected dipeptide Z-GLU-(Bu$^t$)$_5$-TRP-OMe.

Hydrogenation in 50% AcOH over 5% Pd/C at room temperature and atmospheric pressure for two hours affords the acetic salt of the unblocked dipeptide, which is desalified by treatment with iso-Pr$_2$EtN in DMF for 30 minutes, under stirring. Purification affords 0.886 g of the dipeptide H$_2$N-GL U(Bu$^t$)$_5$-TRP-OMe. This is dissolved in DMF and 0.804 g of pGLU-OPCP in DMF are added, stirring the mixture for 34 hours at room temperature. 0.625 g of protected tripeptide pGLU-GLU-(Bu$^t$)$_5$-TRP-OMe is obtained. Treatment with trifluoroacetic acid (TFA) frees the carboxyl group in position 5. Mild basic hydrolysis affords 0.432 g free tripeptide pGLU-GLU-TRP.

Composition: theoretical: C=56.75, H=5.44, N=12.61. Found: C=56.88, H=5.42, N=12.65.

Melting point: 168° C.

EXAMPLE 4

Synthesis of pGLU-ASP-TRP 1 g of tryptophan methylester hydrochloride (TRP-OMe-HCl) in DMF is additioned with 0.4 ml of Et$_3$N and stirred for 30 minutes. The solution is then cooled to −10° C. and treated, in succession, with 1.270 g of Z-ASP(Bu$^t$)$_4$-OH in DMF, 0.530 g of HOBT and 1.238 g of DCCI. The resulting mixture is kept at −10° C. for 3 hours and then at room temperature for another 24 hours. Purification on silica gel affords 1.295 g of protected dipeptide Z-ASP(Bu$^t$)$_4$-TRP-OMe. Hydrogenation in 50% AcOH over 5% Pd/C at room temperature and atmospheric pressure for 2 hours affords the acetic salt of the free dipeptide, which is desalified by treatment with iso-Pr$_2$EtN in DMF for 30 minutes, under stirring. Purification affords 0.869 g of protected dipeptide H$_2$N-ASP(Bu$^t$)$_4$-TRP-OMe. This is dissolved in DMF and treated with 0.820 g of pGLU-OPCP in DMF, stirring the mixture for 36 hours at room temperature. 0.653 g of protected tripeptide pGLU-ASP(Bu$^t$)$_4$-TRP-OMe is obtained. Treatment with TFA frees the carboxyl group in the beta position of the aspartic acid. Mild basic hydrolysis affords 0.468 g of tripeptide pGLU-ASP-TRP.

Composition: theoretical: C=55.81, H=5.15, N=13.01. Found: C=55.90, H=5.20, N=12.98.

Melting point: 232° C.

EXAMPLE 5

Synthesis of pGLU-SER-TRP 1 g of tryptophan methylester hydrochloride (TRP-OMe-HCl) in DMF is additioned with 0.4 ml of Et$_3$N and stirred for 30 minutes. The solution is then cooled to −10° C. and treated, in succession, with 1.158 g of N-Z-O(Bu$^t$)-SER (previously freed from its dicyclohexylammonium salt) and 0.530 of HOBT. After 30 minutes of stirring, the mixture is treated with 1.240 g of DCCI.

The resulting mixture is kept at −10° C. for 3 hours and then at room temperature for another 27 hours. Purification affords 1.051 of protected dipeptide N-Z-O(Bu$^t$)-SER-TRP-OMe. Hydrogenation in 50% AcOH over 5% Pd/C at room temperature and atmospheric pressure for 2 hours affords the acetic salt of the dipeptide, which is desalified by treatment with iso-Pr$_2$EtN in DMF for thirty minutes, under stirring.

0.680 of protected dipeptide H$_2$N-O(Bu$^t$)-SER-TRP-OMe is obtained. This is dissolved in DMF and treated with 0.684 g of pGLU-OPCP in DMF, stirring the mixture for 40 hours at room temperature. Purification affords 0.534 g of protected tripeptide pGLU-O(Bu$^t$)-SER-TRP-OMe is obtained. Treatment with TFA frees the hydroxy group in the serine. Mild basic hydrolyssis affords 0.373 g of tripeptide pGLU-SER-TRP.

Composition: theoretical: C=56.71, H=5.51, N=13.92. Found: C=56.78, H=5.55, N=13.85.

Melting point: 248° C.

EXAMPLE 6

Synthesis of pGLU-ALA-TRP 1 g of pGLU-OPCP in DMF is additioned under stirring with 0.363 g of alanine methylester hydrochloride (ALA-OMe-HCl) dissolved in DMF and 0.5 ml of Et$_3$N. The mixture is stirred for 24 hours at room temperature. Purification affords 0.335 g of dipeptide pGLU-ALA-OMe, which is then reacted with excess hydrazine hydrate to afford 0.280 g of the compound pGLU-ALA-NH-NH$_2$. The corresponding azide pGLU-ALA-N$_3$ is prepared by reaction with isopentylnitrite for 30 minutes at −20° C. The product is reacted 'in situ' with 0.311 g of tryptophan methylester hydrochloride (TRP-OMe HCl) in DMF and 0.14 ml of Et$_3$N, stirring the mixture for 24 hours at room temperature. Purification affords 0.365 g of protected tripeptide pGLU-ALA-TRP-OMe, which upon mild basic hydrolysis affords 0.272 g of free tripeptide pGLU-ALA-TRP.

Composition: theoretical: C=59.06, H=5.74, N=14.50. Found: C=59.20, H=5.75, N=14.48.

Melting point: 268° C.

EXAMPLE 7

Synthesis of pGLU-ASN-TRP 1 g of TRP-OMe-HCl in DMF is additioned in succession with iso-Pr$_2$EtN up to a pH of 7.5, and then 0.910 g of N-Boc-ASN-ONP (Boc=tertbutyloxycarbonyl) in DMF, stirring the resulting mixture for 23 hours at room temperature. Purification affords 0.985 g of protected dipeptide N-Boc-ASN-TRP-OMe, which is treated with excess TFA for 20 minutes at room temperature. The excess TFA is removed under vacuum and the peptide salt is dissolved in DMF, bringing the pH to 7.5 with iso-Pr$_2$EtN. The resulting solution is brought to −10° C. and treated with 0.836 g of pGLU-OPCP in DMF. The mixture is stirred vigorously at −10° C. for the first 3 hours, and then at room temperature for the next 19 hours. Purification affords 0.540 g of protected tripeptide pGLU-ASN-TRP-OMe, which upon mild basic hydrolysis affords 0.398 g of free tripeptide pGLU-ASN-TRP.

Composition: theoretical: C=55.94, H=5.40, N=16.30. Found: C=56.00, H=5.45, N=16.22.

Melting point: 215° C.

EXAMPLE 8

Synthesis of pGLU-GLN-TRP 1 g of TRP-OMe-HCl in DMF is additioned in succession with iso-Pr$_2$EtN up to a pH of 7.5, and then 0.967 g of N-Boc-GLU-ONP in DMF, stirring the resulting mixture for 20 hours at room temperature. Purification affords 1.227 g of dipeptide N-Boc-GLN-TRP-OMe, which is treated with excess TFA for 20 minutes at room temperature. The excess TFA is removed under vacuum and the peptide salt is dissolved in DMF, bringing the pH to 7.5 with iso-Pr$_2$EtN. The resulting solution is brought to −10° C. and treated with 1.013 g of pGLU-OPCP in DMF. The mixture is stirred vigorously at −10° C. for the first 3 hours, and then at room temperature for the next 18 hours. Purification affords 0.737 g of protected tripeptide pGLU-GLN-TRP-OMe, which upon mild basic hydrolysis affords 0.583 g of free tripeptide pGLU-GLN-TRP.

Composition: theoretical: C=56.88, H=5.68, N=15.79. Found: C=56.98, H=5.74, N=15.65.

Melting point: 205° C.

EXAMPLE 9

Synthesis of pGLU-ILE-TRP 1 g of pGLU-OPCP in DMF is additioned under stirring with 0.472 g of ILE-OMe.HCl dissolved in DMF and 0.5 ml of Et$_3$N, and the resulting mixture is stirred for 24 hours at room temperature. Purification affords 0.404 g of dipeptide pGLU-ILE-OMe, which is treated with excess hydrazine hydrate to afford after crystallization the compound pGLU-ILE-NH-NH$_2$. The corresponding azide is prepared by reaction with isopentylnitrite for 30 minutes at −20° C. The azide is reacted 'in situ' with 0.306 g of TRP-OMe.HCl in DMF and 0.15 ml Et$_3$N, and stirred for 24 hours at room temperature. Purification affords 0.392 g of protected tripeptide pGLU-ILE-TRP-OMe, which upon mild basic hydrolysis affords 0.296 g of free tripeptide pGLU-ILE-TRP.

Composition: theoretical: C=60.56, H=6.77, N=13.45. Found: C=60.75, H=6.85, N=13.34.

Melting point: 252° C.

EXAMPLE 10

Synthesis of pGLU-LEU-TRP 1 g of pGLU-OPCP in DMF is additioned under stirring with 0.472 g of LEU-OMe.HCl dissolved in DMF and 0.5 ml of Et$_3$N, and the resulting mixture is stirred for 24 hours at room temperature. Purification affords 0.387 g of dipeptide pGLU-LEU-OMe, which is treated with excess hydrazine hydrate to afford the hydrazine derivative pGLU-LEU-NH-NH$_2$. The corresponding azide is prepared by reaction with isopentylnitrite for 30 minutes at −20° C. The azide is reacted 'in situ' with 0.280 g of TRP-OMe.HCl in DMF and 0.15 ml Et$_3$N, and stirred for 24 hours at room temperature. Purification affords 0.334 g of protected tripeptide pGLU-LEU-TRP-OMe, which upon mild basic hydrolysis affords 0.258 g of free tripeptide pGLU-LEU-TRP.

Composition: theoretical: C=60.56, H=6.77, N=13.45. Found: C=60.89, H=6.83, N=13.55.

Melting point: 250° C.

EXAMPLE 11

Synthesis of pGLU-PRO-TRP 1 g of pGLU-OPCP in DMF is additioned under stirring with 0.439 g of PRO-OMe.HCl dissolved in DMF and 0.5 ml of Et$_3$N, and the resulting mixture is stirred for 24 hours at room temperature. Purification affords 0.325 g of dipeptide pGLU-PRO-OMe, which is treated with excess hydrazine hydrate to afford the compound pGLU-PRO-NH-NH$_2$. The corresponding azide is prepared by reaction with isopentylnitrite for 30 minutes at −20° C. The azide is reacted 'in situ' with 0.267 g of TRP-OMe.HCl in DMF and 0.15 ml Et$_3$N, and stirred for 24 hours at room temperature. Purification affords protected tripeptide pGLU-PRO-TRP-OMe, which upon mild basic hydrolysis affords 0.301 g of free tripeptide pGLU-PRO-TRP.

Composition: theoretical: C=61.16, H=5.86, N=13.58. Found: C=61.18, H=5.83, N=13.46.

Melting point: 255° C.

EXAMPLE 12

Synthesis of pGLU-LYS-TRP 1 g of TRP-OMe.HCl in DMF is additioned in succession with iso-Pr₂EtN up to a pH of 7.5, and then 1.963 g of N-Boc-N-Z-LYSINE-ONP (ONP=orthonitrophenyl) in DMF, stirring the resulting mixture for 20 hours at room temperature. Purification affords 1.319 g of the protected dipeptide, which is treated with excess TFA for 20 minutes at room temperature. The excess TFA is removed under vacuum and the peptide salt is dissolved in DMF, bringing the pH to 7.5 with iso-Pr₂EtN. The resulting solution is brought to −10° C. and treated with 0.884 g of pGLU-OPCP in DMF. The mixture is stirred vigorously at −10° C. for the first 3 hours, and then at room temperature for the next 19 hours. Purification affords 0.870 g of protected tripeptide which is hydrogenated in 50% AcOH over 5% Pd/C, at room temperature and atmospheric pressure for 2 hours. Mild basic hydrolysis affords 0.524 g of free tripeptide pGLU-LYS-TRP.

Composition: theoretical: C=59.58, H=6.59, N=15.78. Found: C=59.40, H=6.40, N=15.65.

Melting point: 228° C.

EXAMPLE 13

Synthesis of pGLU-ARG-TRP 1 g of TRP-OMe.HCl in DMF plus 0.4 ml of Et₃N, is stirred for 30 minutes, cooled to −10° C., and then additioned in succession with 1.252 g of Boc-N-nitroARGININE, 0.530 g of HOBT and 1.24 g of DCCI, under stirring. The resulting mixture is stirred vigorously for 4 hours at −10° C., and then for 27 hours at room temperature. 1.225 g of protected dipeptide are isolated and then treated with excess TFA for 20 minutes at room temperature. The excess TFA is removed under vacuum, and the free dipeptide is taken up in DMF. The resulting solution is treated with 1 g of pGLU-OPCP with stirring, and then stirred for 40 hours at room temperature. Purification affords 0.630 g of blocked tripeptide which is treated in 50% AcOH with 5% Pd/C at room temperature and atmospheric pressure for 2 hours. Mild basic hydrolysis affords 0.394 of pGLU-ARG-TRP tripeptide.

Composition: theoretical: C=56.04, H=6.20, N=20.79. Found: C=56.15, H=6.10, N=20.65.

Melting point: 202° C.

EXAMPLE 14

Synthesis of pGLU-LEU-TRP-OEt 1 g of pGLU-OPCP in DMF is additioned under stirring with 0.480 g of LEU-OMe.HCl dissolved in DMF and 0.5 ml of Et₃N. The resulting mixture is stirred for 24 hours at room temperature. Purification affords 302 mg of dipeptide pGLU-LEU-OMe, which is reacted with excess hydrazine hydrate to obtain the hydrazine derivative pGLU-LEU-NH-NH₂. The corresponding azide is prepared by reaction with isopentylnitrite for 30 minutes at −20° C. The azide is then treated with 250 mg of TRP-OEt.HCl in DMF and 0.15 ml of Et₃N and stirred for 24 hours at room temperature. Purification affords 0.274 g of the blocked tripeptide pGLU-LEU-TRP-OEt.

Composition: theoretical: C=62.15, H=7.25, N=12.60. Found: C=62.28, H=7.29, N=12.51.

Melting point: 180° C.

PHARMACOLOGICAL ACTIVITY

Animal tests were run to determine the pharmacological effects of the compounds according to the present invention.

HYPOTENSIVE EFFECT OF THE COMPOUNDS

Male CD Charles River rats weighing 220–250 g were used, anesthetized with ethyl urethane (1.75 g/kg intraperitoneally). After incannulation of the trachea, the right carotid was isolated and connected by a cannula to a pressure measurement device. The isolated left carotid was used to record the flow by means of an electromagnetic flussimeter. Other parameters recorded were: dp/dt, ECG (electrocardiogram), BPM (beats per minute). All values were recorded on an 8 channel Hewlett Packard polygraph.

The tripeptides were dissolved in 0.9% NaCl and injected in the right femoral vein.

The results are reported in the following table which gives the lowering of the minimum and maximum pressure obtained upon administration of the drug.

TABLE

Hypotensive effect of the peptides and derivatives in a dose of 2 mg/kg

| Compound | Δ on minimum (in mm Hg) | Δ on maximum (in mm Hg) |
|---|---|---|
| pGLU—GLY—TRP | 35 | 25 |
| pGLU—GLU—TRP | 10 | 20 |
| pGLU—ASP—TRP | 10 | 10 |
| pGLU—SER—TRP | 35 | 45 |
| pGLU—ALA—TRP | 20 | 10 |
| pGLU—ASN—TRP | 20 | 35 |
| pGLU—GLN—TRP | 10 | 20 |
| pGLU—LEU—TRP | 30 | 30 |
| pGLU—LYS—TRP | 25 | 35 |
| pGLU—ARG—TRP | 15 | 25 |
| pGLU—LEU—TRP—OEt | 20 | 30 |
| pGLU—ILE—TRP—OEt | 25 | 30 |

EXAMPLE 15

Potentiation of adenosine with pGLU-GLU-TRP

Any interference of synthesized peptides with the hemodynamic effects of adenosine would be shown using the method described. Injected in a dose of 0.15 mg/kg in the vein, this substance shows a transient hypotensive effect. In this case the compound according to the invention was pGLU-GLU-TRP.

Results: Administration of pGLU-GLU-TRP in a dose of 0.1 mg/kg in the vein, 15 minutes before administration of adenosine, potentiates and prolongs the hypotensive effect.

EXAMPLE 16

Potentiation of adenosine with pGLU-ASN-TRP

The tripeptide pGLU-ASN-TRP was tested using the method described.

Results: When injected in the vein in a 0.1 mg/kg dose 15 minutes before administration of adenosine, the compound potentiates and prolongs the hypotensive effect.

EXAMPLE 17

Analgesic activity of pGLU-ASN-TRP

This activity was evaluated with the writhing test, using a 3% aqueous acetic acid solution as pain-causing agent, injected intraperitoneally (0.1 ml/10 g). The experiment was performed with 80 female Swiss albino mice weighing 18–24 g, fasting for three hours and divided into groups of 20 animals each:

(1) controls, treated with 0.9% NaCl;
(2) those treated with the test tripeptide (10 mg/kg intraperitoneally);
(3) those treated with adenosine (2 mg/kg intraperitoneally);
(4) those treated with the tripeptide (10 mg/kg intraperitoneally) and adenosine (2 mg/kg intraperitoneally).

In groups 1 and 2 the substances were administered 40 minutes before the acetic acid; in group 3 the adenosine was administered 10 minutes before the acetic acid; in group 4 the adenosine was administered 30 minutes after the tripeptide and 10 minutes before the acetic acid. After the acetic acid innoculation, the animals were placed in groups of 5 in plastic cages, and observed for a 20 minute period. The number of contorsions the animals made during that period was recorded. Based on the mean reduction of the number of contorsions of the treated animals with respect to the controls, the analgesic action of the test substance was calculated.

Results: Adenosine alone showed an analgesic activity of 20%. The tripeptide pGLU-ASN-TRP showed analgesic activity of 25%. Adenosine and tripeptide together showed an additive effect.

The compounds according to the present invention were shown to have no particular toxic effects, at least in the range of therapeutic dosages. This would seem logical since these compounds in the animal organism may be easily transformed into physiological substances (the L-amino acids starting materials).

They may be used clinically in a therapeutically effective quantity in the form of pharmaceutical fromulations. These pharmaceutical formulations according to the present invention may be used for oral administration as, for example, lozenges, capsules, powders, drops or syrups, possibly in gastric-resistant formulations, or for perenteral administration in the form of injectable solutions, with the aid of pharmaceutically compatible carriers and/or excipients. The dose (with reference to the pure compound) for the above mentioned administration route is preferably as follows:

(a) 150 to 300 mg orally;
(b) 20 to 40 mg intramuscularly;
(c) 4 to 9 mg intravenously.

The following is a non-limiting example of a formulation:

lyophilate ampul:
20 mg peptide
50 mg mannitol
2 mg sodium chloride
solvent ampul:
2 ml twice distilled water.

We claim:

1. Tripeptide compounds in a substantially pure form, formed by levorotatory amino acids of the formula p-GLU-X-TRP wherein X is a radical derived from an amino acid chosen from the group GLY, VAL, GLU, ASP, SER, ALA, PRO, LYS, ARG, ILE, LEU, bonded to p-GLU-TRP and by a peptide bond.

2. Lower alkyl tryptophan esters of tripeptide compounds formed by levorotatory amino acids of formula p-GLU-X-TRP wherein X is a radical derived from an amino acid chosen from the group GLY, VAL, GLU, ASP, SER, ALA, ASN, GLN, ILE, LEU, PRO, LYS and ARG, bonded to p-GLU-TRP and by a peptide bond.

3. A lower alkyl tryptophan ester according to claim 2 wherein X is other than ASN or GLN.

4. The compounds according to claim 2, wherein said lower alkyl is methyl or ethyl.

5. A method of reducing tension and pain in mammals comprising administering to said mammals a hypotensive and analgesic amount of a tripeptide, made from levorotatory amino acids of formula p-GLU-X-TRP wherein X is a radical derived from an amino acid chosen from the group GLY, VAL, GLU, ASP, SER, ALA, ASN, GLN, ILE, LEU, PRO, LYS and ARG, bonded to p-GLU-TRP and by a peptide bond, or a lower alkyl tryptophan ester thereof.

6. A method according to claim 5 wherein the compound is p-GLU-ASN-TRP.

7. A method according to claim 5 comprising reducing tension by administering the tripeptide.

8. A pharmaceutical composition comprising a hypotensive and analgesic effective amount of a tripeptide, made from levorotatory amino acids of formula p-GLU-X-TRP wherein is a radical derived from an amino acid chosen from the group GLY, VAL, GLU, ASP, SER, ALA, ASN, GLN, ILE, LEU, PRO, LYS and ARG, bonded to p-GLU-TRP and by a peptide bond, or a lower alkyl tryptophan ester thereof.

9. A pharmaceutical composition according to claim 8 containing a hypotensive effect amount of the tripeptide.

10. A pharmaceutical composition according to claim 9 wherein the tripeptide is p-GLU-ASN-TRP.

* * * * *